United States Patent
Choi et al.

(10) Patent No.: US 11,786,179 B2
(45) Date of Patent: Oct. 17, 2023

(54) BIO-SIGNAL MEASURING APPARATUS

(71) Applicant: SAMSUNG ELECTRONICS CO., LTD., Suwon-si (KR)

(72) Inventors: Chang Mok Choi, Suwon-si (KR); Byung Hoon Ko, Hwaseong-si (KR); Young Soo Kim, Seoul (KR); Jong Wook Lee, Suwon-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1047 days.

(21) Appl. No.: 16/250,601

(22) Filed: Jan. 17, 2019

(65) Prior Publication Data

US 2019/0216399 A1 Jul. 18, 2019

(30) Foreign Application Priority Data

Jan. 18, 2018 (KR) .................. 10-2018-0006755

(51) Int. Cl.
*A61B 5/00* (2006.01)
*A61B 5/024* (2006.01)

(52) U.S. Cl.
CPC ........ *A61B 5/6843* (2013.01); *A61B 5/02416* (2013.01); *A61B 5/02427* (2013.01); *A61B 5/7445* (2013.01); *A61B 5/6898* (2013.01); *A61B 2562/0261* (2013.01); *A61B 2562/166* (2013.01)

(58) Field of Classification Search
CPC ............. A61B 5/6843; A61B 5/02416; A61B 5/02427; A61B 5/7445; A61B 5/6898; A61B 2562/0261; A61B 2562/166; A61B 5/021; A61B 5/0059; A61B 5/7225; A61B 2562/16; A61B 2090/065; A61B 5/02; A61B 5/145

See application file for complete search history.

(56) References Cited

U.S. PATENT DOCUMENTS

| | | |
|---|---|---|
| 8,761,853 B2 | 6/2014 | Thaveeprungsriporn et al. |
| 9,072,439 B2 | 7/2015 | Kassim et al. |
| 9,480,407 B2 | 11/2016 | Kumar et al. |
| 9,538,927 B2 | 1/2017 | Thaveeprungsriporn et al. |
| 9,737,220 B2 | 8/2017 | Kim et al. |
| 9,918,647 B2 | 3/2018 | Kang et al. |

(Continued)

FOREIGN PATENT DOCUMENTS

| | | |
|---|---|---|
| JP | 2007-209374 A | 8/2007 |
| JP | 2009-66042 A | 4/2009 |

(Continued)

OTHER PUBLICATIONS

Communication dated Aug. 17, 2022 issued by the Korean Intellectual Property Office in Korean Application No. 10-2018-0006755.

*Primary Examiner* — Eric F Winakur
*Assistant Examiner* — Abid A Mustansir
(74) *Attorney, Agent, or Firm* — Sughrue Mion, PLLC

(57) ABSTRACT

A bio-signal measuring apparatus includes: a substrate; a pulse wave measurer provided at the substrate and configured to measure pulse waves of a subject; and a pressure measurer provided at the substrate and configured to measure a contact pressure between the subject and the pulse wave measurer.

19 Claims, 21 Drawing Sheets

(56) References Cited

U.S. PATENT DOCUMENTS

| | | | |
|---|---|---|---|
| 10,874,348 B1* | 12/2020 | Han | A61B 5/6843 |
| 2008/0228089 A1* | 9/2008 | Cho | A61B 5/02125 |
| | | | 600/485 |
| 2010/0076282 A1* | 3/2010 | Sandmore | A61B 5/6843 |
| | | | 600/587 |
| 2012/0190944 A1 | 7/2012 | Thaveeprungsriporn et al. | |
| 2013/0085356 A1* | 4/2013 | Schlottau | A61B 5/6803 |
| | | | 600/323 |
| 2013/0296665 A1 | 11/2013 | Kassim et al. | |
| 2013/0296666 A1 | 11/2013 | Kumar et al. | |
| 2013/0296673 A1 | 11/2013 | Thaveeprungsriporn et al. | |
| 2016/0000339 A1* | 1/2016 | Kang | G01L 11/02 |
| | | | 600/479 |
| 2017/0086743 A1* | 3/2017 | Bushnell | A61B 5/681 |

FOREIGN PATENT DOCUMENTS

| | | | |
|---|---|---|---|
| JP | 2009-201895 A | 9/2009 | |
| JP | 2014-507209 A | 3/2014 | |
| JP | 2015-192702 A | 11/2015 | |
| JP | 5847202 B2 | 1/2016 | |
| KR | 20060116635 A * | 5/2005 | A61B 5/02 |
| KR | 10-2006-0116635 A | 11/2006 | |
| KR | 10-1033472 B1 | 5/2011 | |
| KR | 10-2016-0004829 A | 1/2016 | |
| KR | 10-2017-0006106 A | 1/2017 | |

* cited by examiner

BIO-SIGNAL MEASURING APPARATUS

CROSS-REFERENCE TO RELATED APPLICATION(S)

This application claims priority from Korean Patent Application No. 10-2018-0006755, filed on Jan. 18, 2018, in the Korean Intellectual Property Office, the entire disclosure of which is incorporated herein by reference for all purposes.

BACKGROUND

1. Field

Apparatuses consistent with example embodiments relate to a bio-signal measuring apparatus.

2. Description of the Related Art

Healthcare technology is receiving a lot of attention as society rapidly ages, leading to issues such as the increase in healthcare costs and the like. Accordingly, in addition to medical devices for use in hospitals or examination institutions, small medical devices that individuals can carry are also being developed.

Furthermore, such small medical devices are provided as wearable devices which can be worn by a user to allow the user to directly measure and manage cardiovascular health status such as blood pressure and the like.

Therefore, much research is conducted recently in manufacture of devices for measuring cardiovascular health status, such as blood pressure and the like, in a compact size.

SUMMARY

Example embodiments provide a bio-signal measuring apparatus.

According to an aspect of an example embodiment, there is provided a bio-signal measuring apparatus including: a substrate; a pulse wave measurer provided at the substrate and configured to measure pulse waves of a subject; and a pressure measurer provided at the substrate and configured to measure a contact pressure between the subject and the pulse wave measurer.

The pressure measure may include a strain gauge configured to measure a strain of the substrate, and the pressure measurer may be configured to measure the contact pressure between the subject and the pulse wave measurer based on the strain measured by the strain gauge.

The substrate may be a printed circuit board or a display substrate.

The bio-signal measuring apparatus may further include a housing, wherein an end portion of the substrate is connected to the housing.

The strain gauge may be provided at a position of the substrate that is spaced apart from the pulse wave measurer.

The bio-signal measuring apparatus may further include a housing connected to a bottom surface of the substrate at a plurality of points.

The strain gauge may be provided at a region of the substrate between the plurality of points.

The bio-signal measuring apparatus may further include: a housing; and a plurality of supports provided on a bottom surface of the substrate to form a space between the substrate and the housing, wherein the plurality of supports are configured so that the bio-signal measuring apparatus is detachable from the housing by minimizing horizontal friction between the housing and the bio-signal measuring apparatus.

The strain gauge may be provided at a region of the substrate between the plurality of supports.

A top surface of the pulse wave measurer may be configured to come into direct contact with the subject.

The pulse wave measurer may protrude from a top surface of the substrate.

The pulse wave measurer may include: a light emitter configured to emit light onto the subject; and a light receiver configured to receive light reflected or scattered from the subject to measure the pulse waves of the subject.

According to an aspect of another example embodiment, there is provided a bio-signal measuring apparatus including: a substrate; a pulse wave measurer provided at the substrate and configured to measure pulse waves of a subject; a plate including protruding parts which contact a bottom portion of the substrate; and a pressure measurer provided at the plate and configured to measure a contact pressure between the subject and the pulse wave measurer.

The pressure measurer may include at least one strain gauge configured to measure a strain of the substrate, and the pressure measurer may be configured to measure the contact pressure between the subject and the pulse wave measurer based on the strain measured by the strain gauge.

The substrate may be a printed circuit board or a display substrate.

The plate further may include two holes to facilitate bending of the plate in a uniaxial direction.

The two holes may be formed in parallel on an outside of both ends of the protruding parts.

The at least one strain gauge may be provided between the protruding parts.

The pulse wave measurer may have a top surface configured to come into direct contact with the subject.

The pulse wave measurer may protrude from a top surface of the substrate.

The pulse wave measurer may include: a light emitter configured to emit light onto the subject; and a light receiver configured to receive light reflected or scattered from the subject to measure the pulse waves of the subject.

BRIEF DESCRIPTION OF THE DRAWINGS

The above and/or other aspects will become apparent and more readily appreciated from the following description of example embodiments, taken in conjunction with the accompanying drawings in which.

DETAILED DESCRIPTION

Figure 1:
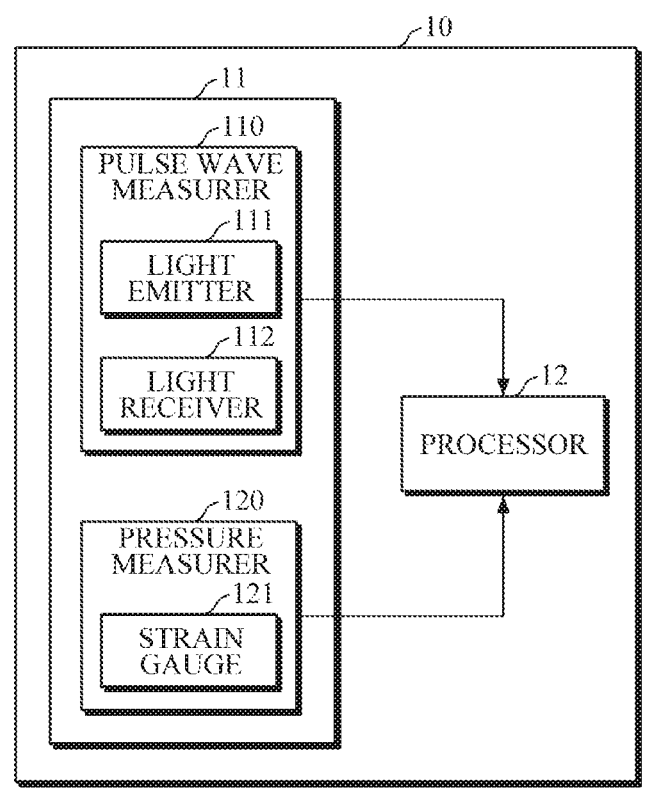
FIG. 1 is a block diagram illustrating a blood pressure measuring apparatus according to an example embodiment.

Hereinafter, example embodiments will be described in detail with reference to the accompanying drawings. It should be noted that, in the drawings, the same reference symbols refer to same parts although illustrated in other drawings. In the following description, a detailed description of known functions and configurations incorporated herein will be omitted when it may obscure the subject matter of the inventive concept.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as "comprising," "including," "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Throughout the drawings and the detailed description, unless otherwise described, the same drawing reference numerals will be understood to refer to the same elements, features, and structures. The relative size and depiction of these elements may be exaggerated for clarity, illustration, and convenience.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

FIG. 1 is a block diagram illustrating a blood pressure measuring apparatus according to an example embodiment. The blood pressure measuring apparatus 10 of FIG. 1 may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device and the wearable device are not limited to the above examples.

Referring to FIG. 1, the blood pressure measuring apparatus 10 includes a bio-signal measurer 11 and a processor 12.

The bio-signal measurer 11 may measure pulse waves of a subject, and a contact pressure between the subject and the bio-signal measurer 11. In this case, the pulse waves may be a photoplethysmogram (PPG).

The bio-signal measurer 11 may include a pulse wave measurer 110 and a pressure measurer 120.

The pulse wave measurer 110 may measure pulse waves of a subject. To this end, the pulse wave measurer may include a light emitter 111 and a light receiver 112.

The light emitter 111 may emit light onto the subject. For example, the light emitter 111 may emit visible light or infrared light onto the subject. However, wavelengths of light emitted by the light emitter 111 may vary depending on the purpose of measurement and the like. Further, the light emitter 111 is not necessarily a single light emitter, and may be an array of a light emitters. In the case where the light emitter 111 is configured as an array of light emitters, each of the light emitters may emit light of a wavelength that is different from that of light emitted by the other light emitters according to the purpose of measurement, or all the light emitters may emit light of the same wavelength. In an example embodiment, the light emitter 111 may be a light emitting diode (LED), a laser diode, or the like. However, this is merely exemplary, and the light emitter 111 is not limited thereto.

The light receiver 112 may measure a pulse wave signal by receiving light reflected or scattered from the subject. In an example embodiment, the light receiver 112 may be a photo diode, a photo transistor (PTr), a charge-coupled device (CCD), or the like. The light receiver 112 is not necessarily a single device, and may be an array of devices.

The pressure measurer 120 may measure strain of a substrate or a plate, which is caused by pressure applied by a subject when pressing the pulse wave measurer 120, and may measure a contact pressure between the subject and the pulse wave measurer 120 based on the measured strain. To this end, the pressure measurer 120 may include a strain gauge 121 formed at the substrate or plate. In an example embodiment, the pressure measurer 120 may use a pressure-strain model which defines a relationship between pressure and a degree of strain of the substrate or plate.

The processor 12 may estimate blood pressure of a subject based on the pulse waves measured by the pulse wave measurer 110 and the contact pressure measured by the pressure measurer 120. In an example embodiment, the processor 12 may estimate blood pressure of the subject by using an oscillometric method which includes measuring a pressure signal while increasing and decreasing pressure, and then estimating blood pressure based on a point where the pressure signal is changed most significantly.

Figure 2:
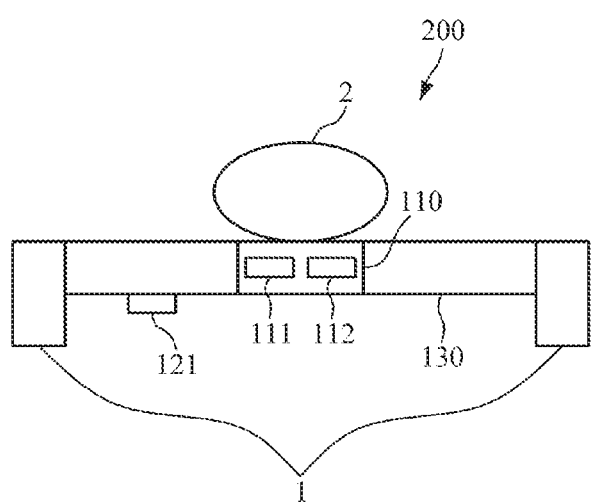
FIG. 2 is a diagram illustrating a structure of a bio-signal measuring apparatus according to another example embodiment.

FIG. 2 is a diagram illustrating a structure of a bio-signal measuring apparatus according to an example embodiment. The bio-signal measuring apparatus 200 of FIG. 2 may be an example of the bio-signal measurer 11 of FIG. 1.

Referring to FIG. 2, the bio-signal measuring apparatus 200 includes a pulse wave measurer 110, a strain gauge 121, and a substrate 130.

The pulse wave measurer 110 may measure pulse waves of a subject 2. To this end, the pulse wave measurer 110 may include a light emitter 111 and a light receiver 112. The light emitter 111 may emit light onto the subject 2, and the light receiver 112 may measure a pulse wave signal by receiving light reflected or scattered from the subject 2. The pulse wave measurer 110 may be provided at a surface of the substrate 130, without protruding from the surface of the substrate 130, so that a top surface of the pulse wave measurer 110, e.g., a top surface, may come into direct contact with the subject 2.

The pulse wave measurer 110 and the strain gauge 121 may be formed at the substrate 130. A structure 1 may be connected to one or more end portions of the substrate 130 to firmly fix the substrate 130. In an example embodiment, the substrate 130 may be a printed circuit board (PCB) or a display substrate.

The strain gauge 121 may measure strain of the substrate 130. The substrate 130 is deformed by pressure applied to the pulse wave measurer 110 by the subject 2, and strain indicates a degree of deformation, such that the strain of the substrate 130 may be used to estimate a contact pressure between the subject 2 and the pulse wave measurer 110.

In an example embodiment, the strain gauge 121 may be formed at the substrate 130 at a position horizontally spaced apart by a predetermined distance from the pulse wave measurer 110. In this case, the predetermined distance may be experimentally obtained by considering a position of the pulse wave measurer 110, to which pressure is applied by the subject 2, and an orientation of the strain of the substrate 130.

The structure 1 may be a structure (e.g., main body or housing of the main body) of an electronic device in which the bio-signal measuring apparatus 200 is installed. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device and the wearable device are not limited to the above examples.

The subject 2 is a subject of which a bio-signal is to be measured, and may be a body part which may come into contact with the pulse wave measurer 110 of the bio-signal measuring apparatus, or a body part of which pulse waves may be measured by using photoplethysmography (PPG). For example, the subject 2 may be an area on a wrist that is adjacent to the radial artery. However, the subject 2 is not limited thereto, and may be distal body portions, such as fingers, toes, earlobes, and the like, which have a high density of blood vessels.

Although FIG. 2 illustrates the strain gauge 121 formed at a bottom portion of the substrate 130, a position of the strain gauge 121 is not limited thereto. That is, the strain gauge 121 may be formed on a top portion of the substrate 130.

Figure 3:
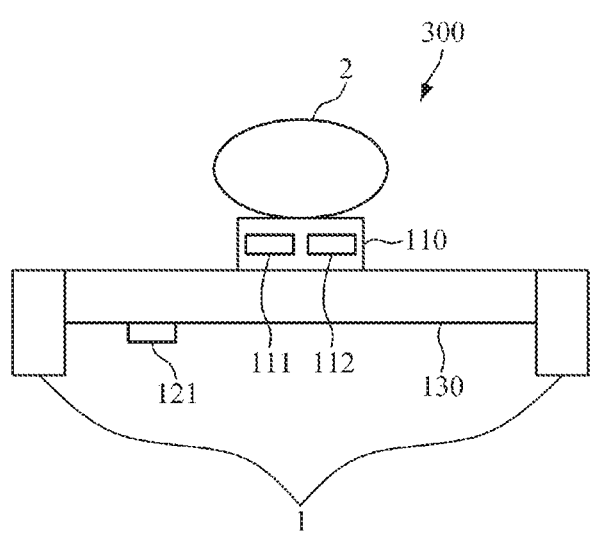
FIG. 3 is a diagram illustrating a structure of a bin-signal measuring apparatus according to another example embodiment.

FIG. 3 is a diagram illustrating a structure of a bio-signal measuring apparatus according to another example embodiment. The bio-signal measuring apparatus 300 of FIG. 3 may be another example of the bio-signal measurer 11 of FIG. 1.

Referring to FIG. 3, the bio-signal measuring apparatus 300 includes a pulse wave measurer 110, a strain gauge 121, and a substrate 130.

The pulse wave measurer 110 may include a light emitter 111, which emits light onto a subject 2, and a light receiver 112 which measures a pulse wave signal by receiving light reflected or scattered from the subject 2. The pulse wave measurer 110 may be provided at the substrate 130 so that a top surface of the pulse wave measurer 110 may protrude higher than a top surface of the substrate 130 to come into direct contact with the subject 2.

The pulse wave measurer 110 and the strain gauge 121 may be formed at the substrate, 130. A structure 1 may be connected to an end portion of the substrate 130 to firmly fix the substrate 130. In an example embodiment, the substrate 130 may be a PCB or a display substrate.

The strain gauge 121 may measure strain of the substrate 130. The strain gauge 121 may be formed at the substrate 130 at a position horizontally spaced apart by a predetermined distance from the pulse wave measurer 110. In this case, the predetermined distance may be experimentally obtained by considering a position of the pulse wave measurer 110, to which pressure is applied by the subject 2, and an orientation of the strain of the substrate 130.

Although FIG. 3 illustrates the strain gauge 121 formed at a bottom portion of the substrate 130, a position of the strain gauge 121 is not limited thereto. That is, the strain gauge 121 may be formed on a top portion of the substrate 130.

Figure 4:
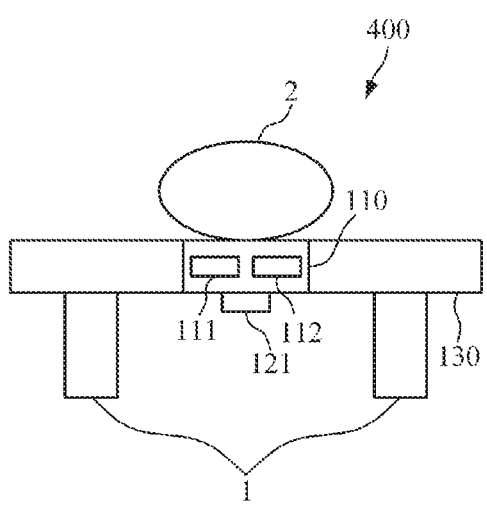
FIG. 4 is a diagram illustrating a structure of a bio-signal measuring apparatus according to another example embodiment.

FIG. 4 is a diagram illustrating a structure of a bio-signal measuring apparatus according to another example embodiment. The bio-signal measuring apparatus 400 of FIG. 4 may be yet another example of the bio-signal measurer 11 of FIG. 1.

Referring to FIG. 4, the bio-signal measuring apparatus 400 includes a pulse wave measurer 110, a strain gauge 121, and a substrate 130.

The pulse wave measurer 110 may include a light emitter 111, which emits light onto a subject 2, and a light receiver 112 which measures a pulse wave signal by receiving light reflected or scattered from the subject 2. The pulse wave measurer 110 may be provided at a surface of the substrate 130, without protruding from the surface of the substrate 130, so that the top surface of the pulse wave measurer 110 may come into direct contact with the subject 2.

The pulse wave measurer 110 and the strain gauge 121 may be formed at the substrate 30. A structure 1 may be connected to the substrate 130 at a plurality of points on a bottom surface of the substrate 130 to firmly fix the substrate 130. In an example embodiment, the substrate 130 may be a PCB or a display substrate.

The strain gauge 121 may measure strain of the substrate 130. In an example embodiment, the strain gauge 121 may be formed at a region of the substrate 130 between the plurality of points where the structure 1 is connected.

Although FIG. 4 illustrates the strain gauge 121 formed at a bottom portion of the substrate 130, a position of the strain gauge 121 is not limited thereto. That is, the strain gauge 121 may be formed on a top portion of the substrate 130.

Figure 5:
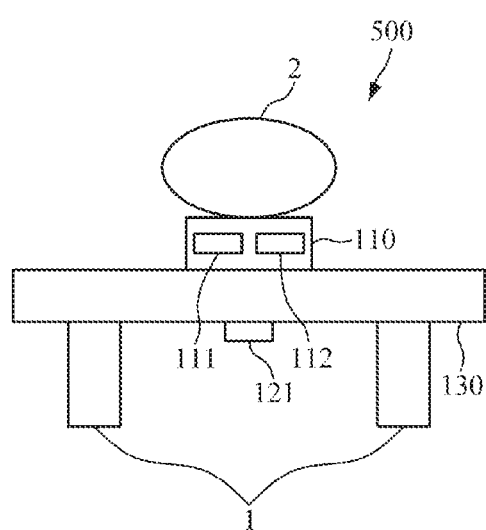
FIG. 5 is a diagram illustrating a structure of a bio-signal measuring apparatus according to another example embodiment.

FIG. 5 is a diagram illustrating a structure of a bio-signal measuring apparatus according to another example embodiment. The bio-signal measuring apparatus 500 of FIG. 5 may be yet another example of the bio-signal measurer 11 of FIG. 1.

Referring to FIG. 5, the bio-signal measuring apparatus 500 includes a pulse wave measurer 110, a strain gauge 121, and a substrate 130.

The pulse wave measurer 110 may include a light emitter 111, which emits light onto a subject 2, and a light receiver 112 which measures a pulse wave signal by receiving light reflected or scattered from the subject 2. The pulse wave measurer 110 may be provided at the substrate 130 so that a top surface of the pulse wave measurer 110 protrudes higher than a top surface of the substrate 130 to come into direct contact with the subject 2.

The pulse wave measurer 110 and the strain gauge 121 may be formed at the substrate 130. A structure 1 may be connected to the substrate 130 at a plurality of points on a bottom surface of the substrate 130 to firmly fix the substrate 130. In an example embodiment, the substrate 130 may be a PCB or a display substrate.

The strain gauge 121 may measure strain of the substrate 130. In an example embodiment, the strain gauge 121 may be formed at a region of the substrate 130 between the plurality of points where the structure 1 is connected.

Although FIG. 5 illustrates the strain gauge 121 formed at a bottom portion of the substrate 130, a position of the strain gauge 121 is not limited thereto. That is, the strain gauge 121 may be formed on a top portion of the substrate 130.

Figure 6:
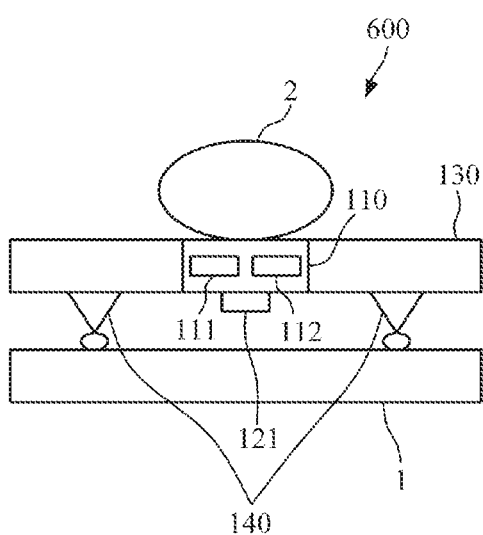
FIG. 6 is a diagram illustrating a structure of a bio-signal measuring apparatus according to another example embodiment.

FIG. 6 is a diagram illustrating a structure of a bio-signal measuring apparatus according to another example embodiment. The bio-signal measuring apparatus 600 of FIG. 6 may be yet another example of the bio-signal measurer 11 of FIG. 1.

Referring to FIG. 6, the bio-signal measuring apparatus 600 includes a pulse wave measurer 110, a strain gauge 121, a substrate 130, and a plurality of supports 140.

The pulse wave measurer 110 may include a light emitter 111, which emits light onto a subject 2, and a light receiver 112 which measures a pulse wave signal by receiving light reflected or scattered from the subject 2. The pulse wave measurer 110 may be provided at the substrate 130, without protruding from a surface of the substrate 130, so that the top surface of the pulse wave measurer 110 may come into direct contact with the subject 2.

The pulse wave measurer 110, the strain gauge 121, and the plurality of supports 140 may be formed at the substrate 130. In an example embodiment, the substrate 130 may be a PCB or a display substrate.

The strain gauge 121 may measure strain of the substrate 130. In an example embodiment, the strain gauge 121 may be formed at a region of the substrate 130 between the plurality of supports 140.

The plurality of supports 140 may be formed on a bottom surface of the substrate 130 to form a space between the substrate 130 and the structure 1. The plurality of supports 140 may be configured so that the bio-signal measuring apparatus 600 may be detachable from the structure 1 by minimizing horizontal friction between the structure 1 and the bio-signal measuring apparatus 600.

Although FIG. 6 illustrates the strain gauge 121 formed at a bottom portion of the substrate 130, a position of the strain gauge 121 is not limited thereto. That is, the strain gauge 121 may be formed on a top portion of the substrate 130.

Figure 7:
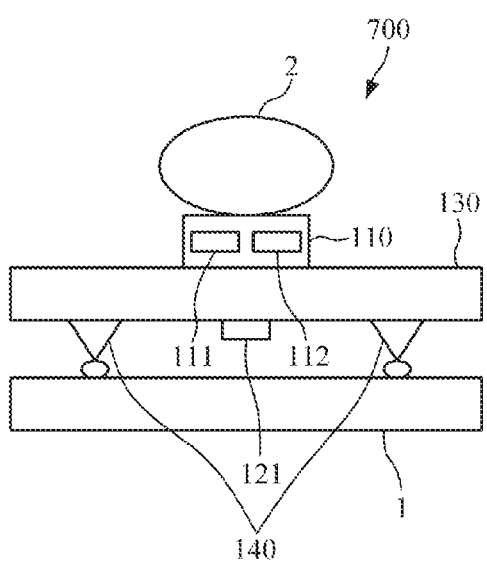
FIG. 7 is a diagram illustrating a structure of a bin-signal measuring apparatus according to another example embodiment.

FIG. 7 is a diagram illustrating a structure of a bio-signal measuring apparatus according to another example embodiment. The bio-signal measuring apparatus 700 of FIG. 7 may be still another example of the bio-signal measurer 11 of FIG. 1.

Referring to FIG. 7, the bio-signal measuring apparatus 700 includes a pulse wave measurer 110, a strain gauge 121, a substrate 130, and a plurality of supports 140.

The pulse wave measurer 110 may include a light emitter 111, which emits light onto a subject 2, and a light receiver 112 which measures a pulse wave signal by receiving light reflected or scattered from the subject 2. The pulse wave measurer 110 may be provided at the substrate 130 so that a top surface of the pulse wave measurer 110 protrudes higher than a top surface of the substrate 130 to come into direct contact with the subject 2.

The pulse wave measurer 110, the strain gauge 121, and the plurality of supports 140 may be formed at the substrate 130. In an example embodiment, the substrate 130 may be a PCB or a display substrate.

The strain gauge 121 may measure strain of the substrate 130. In an example embodiment, the strain gauge 121 may be formed at a region of the substrate 130 between the plurality of supports 140.

The plurality of supports 140 may be formed on a bottom surface of the substrate 130 to form a space between the substrate 130 and the structure 1. The plurality of supports 140 may be configured so that the bio-signal measuring apparatus 700 may be detachable from the structure by minimizing horizontal friction between the structure 1 and the bio-signal measuring apparatus 700.

Although FIG. 7 illustrates the strain gauge 121 formed at a bottom portion of the substrate 130, a position of the strain gauge 121 is not limited thereto. That is, the strain gauge 121 may be formed on a top portion of the substrate 130.

Figure 8:
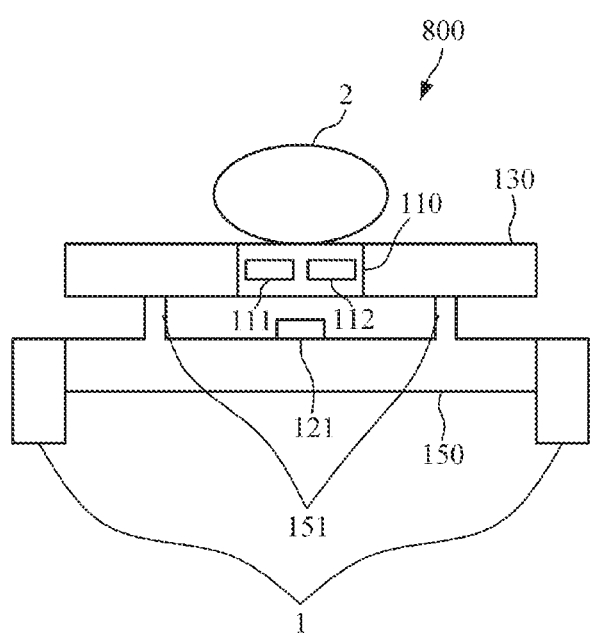
FIG. 8 is a diagram illustrating a structure of a bio-signal measuring apparatus according to another example embodiment.

FIG. 8 is a diagram illustrating a structure of a bio-signal measuring apparatus according to another example embodiment. The bio-signal measuring apparatus 800 of FIG. 8 may be yet another example of the bio-signal measurer 11 of FIG. 1.

Referring to FIG. 8, the bio-signal measuring apparatus 800 includes a pulse wave measurer 110, a strain gauge 121, a substrate 130, and a plate 150.

The pulse wave measurer 110 may include a light emitter 111, which emits light onto a subject 2, and a light receiver 112 which measures a pulse wave signal by receiving light reflected or scattered from the subject 2. The pulse wave measurer 110 may be provided at the substrate 130, without protruding from a surface of the substrate 130, so that the top surface of the pulse wave measurer 110 may come into direct contact with the subject 2.

The pulse wave measurer 110 may be formed at the substrate 130. In an example embodiment, the substrate 130 may be a PCB or a display substrate.

The plate 150 may include a protruding part 151. The plate 150 may come into surface contact or point contact with the substrate 130 through the protruding part 151. In an example embodiment, the plate 150 may include a plurality of holes to facilitate bending of the plate 150, which is caused by force acting on the substrate 130, to be performed in a uniaxial direction.

A structure 1 may be connected to both ends of the plate 150 to firmly fix the plate 150.

A specific structure of the plate 150 will be described below with reference to FIGS. 8, 9, 10, and 11.

The strain gauge 121 is formed at the plate 150 and may measure strain of the plate 150. Pressure applied by the subject 2 to press the pulse wave measurer 110 is transmitted from the substrate 130 to the plate 150 through the protruding part 151 such that the plate 150 is deformed by force transmitted to the plate 150, and strain indicates a degree of deformation. As such, the strain of the plate 150 may be used to estimate a contact pressure between the subject 2 and the pulse wave measurer 110. In an example embodiment, one or more strain gauges 121 may be formed at a region of the plate 150 between the protruding parts 151.

Although FIG. 8 illustrates the strain gauge 121 is formed at a top portion of the plate 150, a position of the strain gauge 121 is not limited thereto. That is, the strain gauge 121 may be formed on a bottom portion of the substrate 130.

Figure 9A:
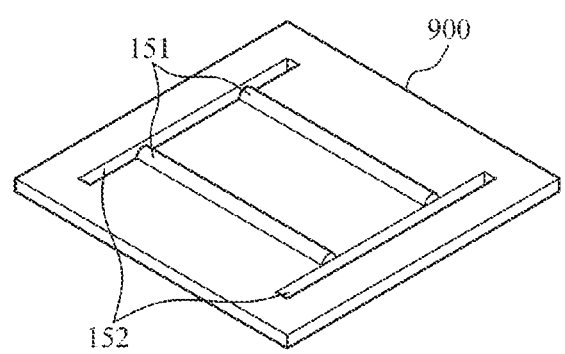
FIG. 9A is a diagram illustrating a structure of a plate according to an example embodiment.
Figure 9B:
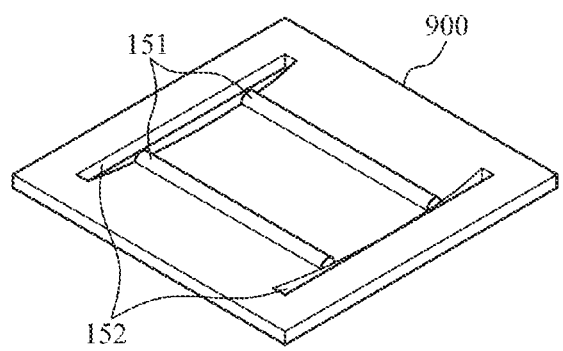
FIG. 9B is an example diagram illustrating a case where a plate is bent.

FIG. 9A is a diagram illustrating a structure of a plate according to an example embodiment, and FIG. 9B is an example diagram illustrating a case where a plate is bent. The plate 900 of FIG. 9A may be an example of the plate 150 of FIG. 8.

Referring to FIGS. 9A and 9B, the plate 900 may include two protruding parts 151 and two holes 152. The protruding parts 151 may have a convex cross-sectional shape.

The two protruding parts 151 are arranged in parallel at a predetermined interval on a top portion of the plate 900, and two holes 152 may be formed as slits arranged in parallel on the outside of both ends of the two protruding parts 151 so that the plate 150 may be bent in a uniaxial direction. In this case, the length of each of the two holes 152 may be longer than a distance between the two protruding parts 151.

Figure 10:
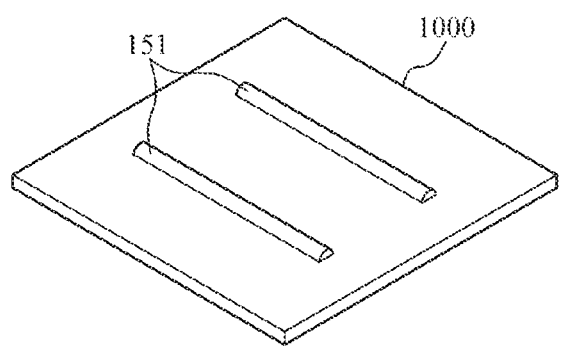
FIG. 10 is a diagram illustrating a structure of a plate according to another example embodiment.

FIG. 10 is a diagram illustrating a structure of a plate according to another example embodiment. The plate 1000 of FIG. 10 may be another example of the plate 150 of FIG. 8.

Referring to FIG. 10, the plate 1000 may include two protruding parts 151. That is, the plate 1000 of FIG. 10 may have a structure similar to the plate 900 of FIG. 9 except that the two holes 152 of the plate 900 of FIG. 9 are omitted. The protruding parts 151 may have a convex cross-sectional shape.

In this case, when a force is transmitted to the plate 150 through the two protruding parts 151, the plate 150 may be bent in a multiaxial direction. Accordingly, in the case where the plate 1000 of FIG. 10 is applied to the bio-signal measuring apparatus 800 of FIG. 8, two or more strain gauges 121 may be formed between the two protruding parts 151 of the plate 150. By using two or more strain gauges 121, an orientation of the strain may be determined accurately as compared to a case of using one strain gauge, such that a contact pressure between the subject 2 and the pulse wave measurer 110 may be estimated more accurately.

Figure 11:
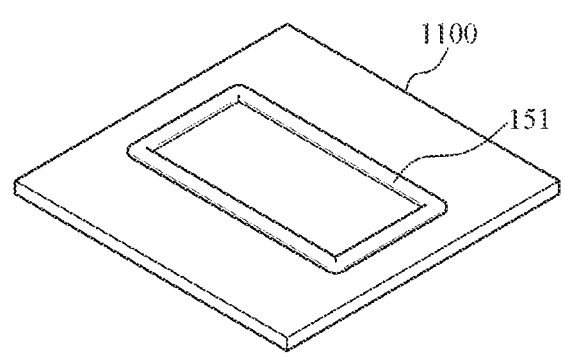
FIG. 11 is a diagram illustrating a structure of a plate according to another example embodiment.

FIG. 11 is a diagram illustrating yet another example of a structure of a plate. The plate 1100 of FIG. 11 may be another example of the plate 150 of FIG. 8.

Referring to FIG. 11, the plate 1100 may include one protruding part 151 having a rectangular shape.

In this case, once force is transmitted to the plate 150 through the rectangular protruding part 151, the plate 150 may bent in a multiaxial direction. Accordingly, in the case where the plate 1100 of FIG. 11 is applied to the bio-signal measuring apparatus 800 of FIG. 8, two or more strain gauges 121 may be formed between the two protruding parts 151 of the plate 150. By using two or more strain gauges 121, an orientation of the strain may be determined accurately as compared to a case of using one strain gauge, such that a contact pressure between the subject 2 and the pulse wave measurer 110 may be estimated more accurately.

Although FIG. 11*illustrates* the plate 1100 having one rectangular protruding part 151, this is merely an example and the shape of the protruding part 151 is not limited thereto. That is, the protruding part 151 may have a circular shape, a triangular shape, or another shape.

Figure 12:
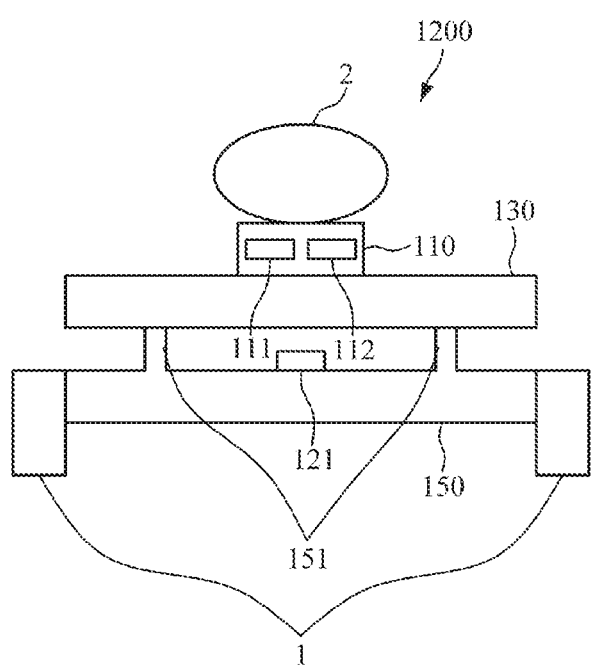
FIG. 12 is a diagram illustrating a structure of a bio-signal measuring apparatus according to another example embodiment.

FIG. 12 is a diagram illustrating a structure of a bio-signal measuring apparatus according to another example embodiment. The bio-signal measuring apparatus 1200 of FIG. 12 may be yet another example of the bin-signal measurer 11 of FIG. 1.

Referring to FIG. 12, the bio-signal measuring apparatus 800 includes a pulse wave measurer 110, a strain gauge 121, a substrate 130, and a plate 150.

The pulse wave measurer 110 may include; a light emitter 111, which emits light onto a subject 2, and a light receiver 112 which measures a pulse wave signal by receiving light reflected or scattered from the subject 2. The pulse wave measurer 110 may be provided at the substrate 130 so that a top surface of the pulse wave measurer 110 protrudes higher than a top surface of the substrate 130 to come into direct contact with the subject 2.

The pulse wave measurer 110 may be formed at the substrate 110. In an example embodiment, the substrate 130 may be a PCB or a display substrate.

The plate 150 may include a protruding part 151. The plate 150 may come into surface contact or point contact with the substrate 130 through the protruding part 151. In an example embodiment, the plate 150 may include a plurality of holes to facilitate bending of the plate 150, which is caused by force acting on the substrate 130, to be performed in a uniaxial direction.

A structure 1 may be connected to both ends of the plate 150 to firmly fix the plate 150.

The strain gauge 121 is formed at the plate 150 and may measure a strain of the plate 150. Pressure applied by the subject 2 to the pulse wave measurer 110 is transmitted from the substrate 130 to the plate 150 through the protruding part 151 so that the plate 150 is deformed by force transmitted to the plate 150, and a strain indicates a degree of deformation, such that the strain of the plate 150 may be used to estimate a contact pressure between the subject 2 and the pulse wave measurer 110. In an example embodiment, one or more strain gauges 121 may be formed at a region of the plate 150 between the protruding parts 151.

Although FIG. 12 illustrates the strain gauge 121 formed at a top portion of the plate 150, a position of the strain gauge 121 is not limited thereto. That is, the strain gauge 121 may be formed on a bottom portion of the plate 150.

Figure 13:
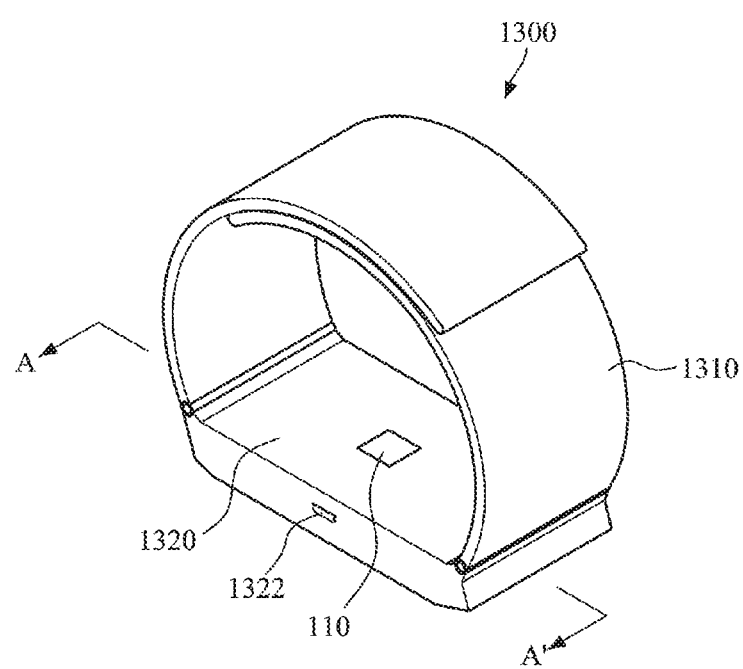
FIG. 13 is a perspective diagram illustrating a wrist-type wearable device according to an example embodiment.
Figure 14A:
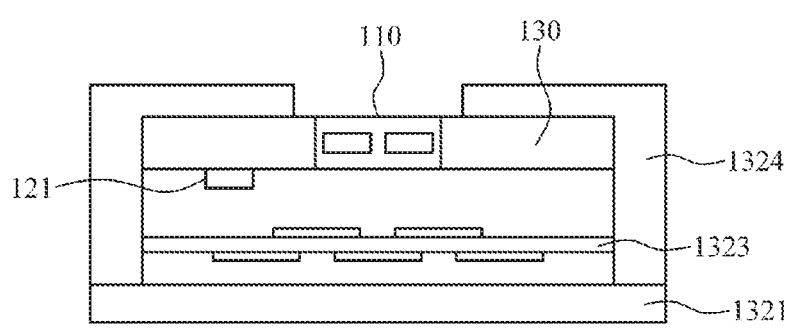
FIGS. 14A, 14B, and 14C are examples of cross-sectional diagrams taken along line A-A' of FIG. 13.
Figure 14B:
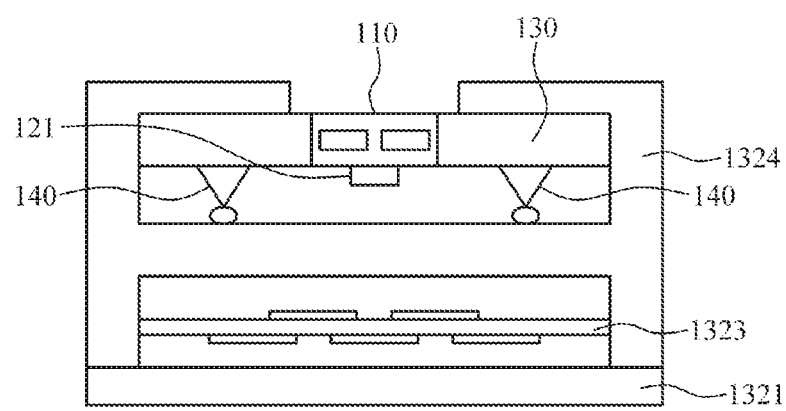
Figure 14C:
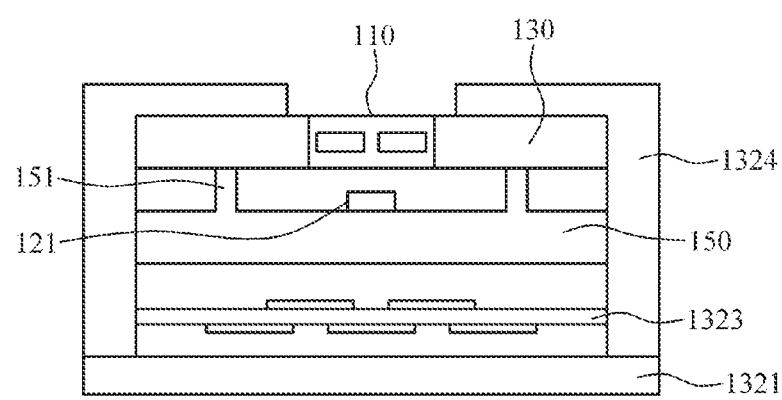

FIG. 13 is a perspective diagram illustrating a wrist-type wearable device according to another example embodiment. FIGS. 14A, 14B, and 14C are examples of cross-sectional diagrams taken along line A-A' of FIG. 13. More specifically, FIG. 14A is a cross-sectional diagram illustrating a case where the bio-signal measuring apparatus 200 of FIG. 2 is embedded in a wrist-type wearable device; FIG. 14B is a cross-sectional diagram illustrating a case where the bio-signal measuring apparatus 600 of FIG. 6 is embedded in a wrist-type wearable device; and FIG. 14C is a cross-sectional diagram illustrating a case where the bio-signal measuring apparatus 800 of FIG. 8 is embedded in a wrist-type wearable device.

Referring to FIGS. 13, 14A, 14B, and 14C, a wrist-type wearable device 1300 includes a strap 1310 and a main body 1320.

The strap 1310 may be connected at both sides of the main body 1320, and both ends of the strap 1310 may be detachably connected or may be integrally formed as a smart band strap. The strap 1310 may be made of a flexible material to wrap around a user's wrist so that the wrist-type wearable device 1300 may be worn around a user's wrist with the main body 1320 contacting the user's wrist.

The main body 1320 may include the above-described blood pressure measuring apparatus 10 and/or the bio-signal measuring apparatuses 200, 300, 400, 500, 600, 700, 800, and 1200 in a housing 1324. For example, as illustrated in FIG. 14A, the main body 1320 may include, in the housing 1324, the substrate 130 having the pulse wave measurer 110 and the strain gauge 121. As illustrated in FIG. 14B, the main body 1320 may include, in the housing 1324, the substrate 130 having the pulse wave measurer 110, the strain gauge 121, and a plurality of supports 140. As illustrated in FIG. 14C, the main body 1320 may include, in the housing 1324, the substrate 130 having the pulse wave measurer 110 and the plate 150 having the protruding part 151 and the strain gauge 121.

The cross-sectional diagrams of FIGS. 14A, 14B, and 14C are merely examples, and are not intended to be limiting. That is, the structure of the other above-described bio-signal measuring apparatuses 300, 400, 500, 700, and 1200 may be embodied in the main body 1320 of the wrist-type wearable device 1300 similar to FIGS. 14A, 14B, and 14C. Further, although FIGS. 14A, 14B and 14C illustrate examples where the pulse wave measurer 110 and the substrate 130 are formed lower than a surface of the housing 1324, the height of the pulse wave measurer 110 and the substrate 130 is not limited thereto; and the pulse wave measurer 110 and the substrate 130 may be, formed at the same height as the surface of the housing 1324 or may protrude from the surface of the housing 1324.

Further, the housing 1324 of the main body 1320 may further include a substrate 132:3 having various components, and a battery which supplies power to the wrist-type wearable device 1300, the blood pressure measuring apparatus 10, and the bio-signal measuring apparatuses 200, 300, 400, 500, 600, 700, 800, and 1200.

In an example embodiment, the pulse wave measurer 110 may be provided at a bottom portion of the main body 1320 so as to be exposed to the wrist of a user. In this manner, when a user wears the wrist-type wearable device 1300, the pulse wave measurer 110 may come into contact with the skin of the user. However, this is merely an example, and the pulse wave measurer 110 may be provided in a display area at a top portion of the main body 1320, or in an area other than the display area.

The wrist-type wearable device 1300 may further include a display 1321 and an input part 1322 which are provided at the main body 1320. The display 1321 may display data processed by the wrist-type wearable device 1300, the blood pressure measuring apparatus 10, and the bio-signal measuring apparatuses 200, 300, 400, 500, 600, 700, 800, and 1200, processing result data thereof, and the like. In this case, the display 1321 may be provided as a touch screen to operate not only as an output interface but also as an input interface. The input part 1322 may receive input of various operation inputs from a user.

Figure 15:
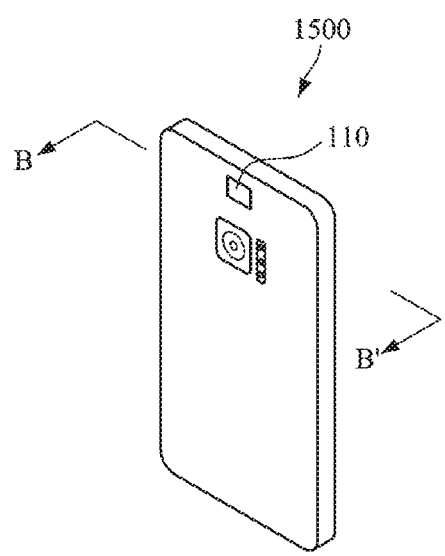
FIG. 15 is a perspective diagram illustrating a mobile device according to another example embodiment.
Figure 16:
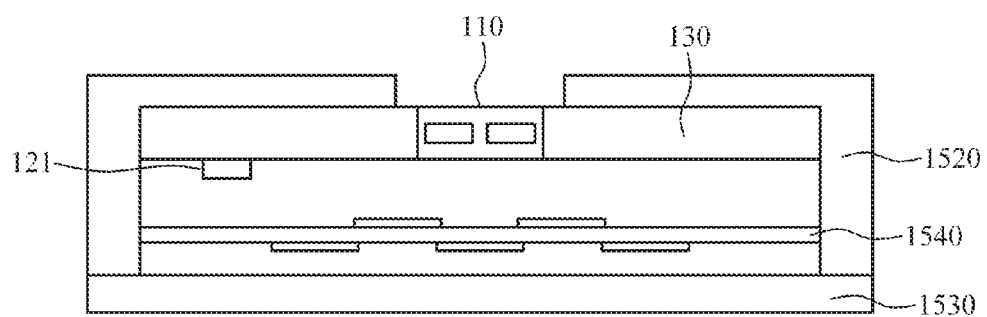
FIG. 16 is an example of a cross-sectional diagram taken along line B-B' of FIG. 15.

FIG. 15 is a perspective diagram illustrating a mobile device according to an example embodiment. FIG. 16 is an example of a cross-sectional diagram taken along line B-B' of FIG. 15. More specifically, FIG. 16 is a cross-sectional diagram illustrating a case where e bio-signal measuring apparatus 200 of FIG. 2 is embedded in a mobile device.

Referring to FIGS. 15 and 16, the mobile device 1500 may include the above-described blood pressure measuring apparatus 10 and/or the bio-signal measuring apparatuses 200, 300, 400, 500, 600, 700, 800, and 1200 in a housing 1520. For example, as illustrated in FIG. 16, the mobile device 1500 may include, in the housing 1520, the substrate 130 having the pulse wave measurer 110 and the strain gauge 121. In this case, the pulse wave measurer 110 may be provided at a rear surface of the mobile device 1500 in such a manner as to be exposed to the outside.

The cross-sectional diagram of FIG. 16 is merely an example and is not intended to be limiting. That is, the structure of the above-described bio-signal measuring apparatuses 200, 300, 400, 500, 600, 700, 800, and 1200 may be reflected similarly to FIG. 16. Further, although FIG. 16 illustrate an example where the pulse wave measurer 110 and the substrate 130 are formed lower than a surface of the housing 1520, the height of the pulse wave measurer 110 and the substrate 130 is not limited thereto; and the pulse wave measurer 110 and the substrate 130 may be formed at the same height as the surface of the housing 1520 or may protrude from the surface of the housing 1520.

Further, the housing 1520 may further include a substrate 1540 having various components, and a battery which supplies power to the mobile device 1500, the blood pressure measuring apparatus 10, and the bio-signal measuring apparatuses 200, 300, 400, 500, 600, 700, 800, and 1200.

The mobile device 1500 may further include a display 1530. The display 1530 may display data processed by the mobile device 1500, the blood pressure measuring apparatus 10, and the bio-signal measuring apparatuses 200, 300, 400, 500, 600, 700, 800, and 1200, processing result data thereof, and the like. In this case, the display 1530 may be provided as a touch screen to operate not only as an output interface but also input interface.

Figure 17:
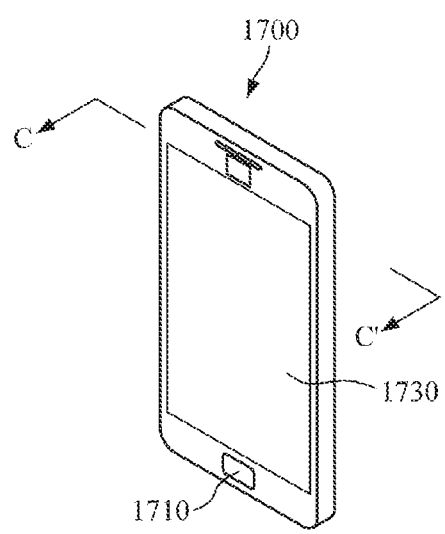
FIG. 17 is a perspective diagram illustrating a mobile device according to another example embodiment.
Figure 18:
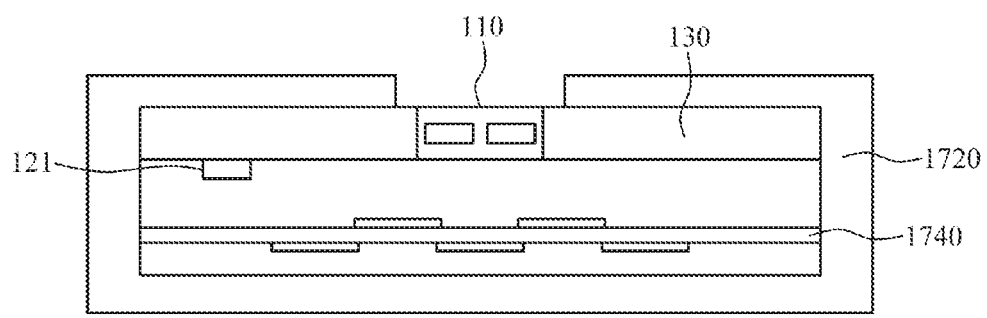
FIG. 18 is an example of a cross-sectional diagram taken along line C-C' of FIG. 17.

FIG. 17 is a perspective diagram illustrating a mobile device according to another example embodiment. FIG. 18 is an example of a cross-sectional diagram taken along line C-C' of FIG. 17. More specifically, FIG. 18 is a cross-sectional diagram illustrating a case where the bio-signal measuring apparatus 200 of FIG. 2 is embedded in a mobile device.

Referring to FIGS. 17 and 18, a mobile device 1700 may include the above-described blood pressure measuring apparatus 10 and/or the bio-signal measuring apparatuses 200, 300, 400, 500, 600, 700, 800, and 1200 in a housing 1720. For example, as illustrated in FIG. 16, the mobile device 1700 may include, in the housing 1720, the substrate 130 having the pulse wave measurer 110 and the strain gauge 121. In this case, the pulse wave measurer 110 may be provided at a front surface of the mobile device 1700 in an area other than an area of a display 1730 in such a manner as to be exposed to the outside.

The cross-sectional diagram of FIG. 18 is merely an example and is not intended to be limiting. That is, the structure of the above-described bio-signal measuring apparatuses 200, 300, 400, 500, 600, 700, 800, and 1200 may be reflected similarly to FIG. 18. Further, although FIG. 18 illustrate an example where the pulse wave measurer 110 and the substrate 130 are formed lower than a surface of the housing 1720, the height of the pulse wave measurer 110 and the substrate 130 is not limited thereto; and the pulse wave measurer 110 and the substrate 130 may be formed at the same height as the surface of the housing 1720 or may protrude from the surface of the housing 1720.

Further, the housing 1720 may further include a substrate 1740 having various components, and a battery which supplies power to the mobile device 1700, the blood pressure measuring apparatus 10, and the bio-signal measuring apparatuses 200, 300, 400, 500, 600, 700, 800, and 1200.

The mobile device 1700 may further include an input part 1710 and the display 1730. The input part 1710 may receive various operation inputs from a user. The display 1730 may display data processed by the mobile device 1700, the blood pressure measuring apparatus 10, and the bio-signal measuring apparatuses 200, 300, 400, 500, 600, 700, 800, and 1200, processing result data thereof, and the like. In this case, the display 1730 may be provided as a touch screen to operate not only as an output interface but also as an input interface.

Embodiments present disclosure can be realized as a computer-readable code written on a non-transitory computer-readable recording medium. Codes and code segments needed for realizing the present disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

Although example embodiments have been described herein, it will be understood by those skilled in the art that various modifications can be made without departing from the inventive concept. Therefore, it is to be understood that that the scope of the inventive concept is not limited to the above-mentioned embodiments, but is intended to include various modifications and equivalents included within the spirit and scope of the appended claims.

What is claimed is:

1. A bio-signal measuring apparatus comprising:
   a substrate;
   a pulse wave sensor provided in direct contact with the substrate and configured to measure pulse waves of a subject;
   a pressure sensor provided at the substrate and configured to measure a contact pressure between the subject and the pulse wave sensor;
   a housing; and
   a plurality of supports provided on a bottom surface of the substrate configured to form a space between the substrate and the housing,
   wherein the plurality of supports are configured so that the substrate is detachable from the housing by minimizing horizontal friction between the housing and the substrate.

2. The bio-signal measuring apparatus of claim 1, wherein the pressure sensor comprises a strain gauge configured to measure a strain of the substrate, and
   the pressure sensor is configured to measure the contact pressure between the subject and the pulse wave sensor based on the strain measured by the strain gauge.

3. The bio-signal measuring apparatus of claim 2, wherein the substrate is a printed circuit board or a display substrate.

4. The bio-signal measuring apparatus of claim 2, wherein an end portion of the substrate is connected to the housing.

5. The bio-signal measuring apparatus of claim 4, wherein the strain gauge is provided at a position of the substrate that is not in contact with the pulse wave sensor.

6. The bio-signal measuring apparatus of claim 2, wherein the housing is connected to a bottom surface of the substrate at a plurality of points.

7. The bio-signal measuring apparatus of claim 6, wherein the strain gauge is provided at a region of the substrate between the plurality of points.

8. The bio-signal measuring apparatus of claim 2, wherein the strain gauge is provided at a region of the substrate between the plurality of supports.

9. The bio-signal measuring apparatus of claim 2, wherein a top surface of the pulse wave sensor is configured to come into direct contact with the subject.

10. The bio-signal measuring apparatus of claim 2, wherein the pulse wave sensor protrudes from a top surface of the substrate.

11. A bio-signal measuring apparatus comprising:
    a substrate;
    a pulse wave sensor provided in direct contact with the substrate and configured to measure pulse waves of a subject;
    a plate comprising protruding parts which contact a bottom portion of the substrate; and
    a pressure sensor provided at the plate and configured to measure a contact pressure between the subject and the pulse wave sensor;
    wherein the plate further comprises two holes to facilitate bending of the plate in a uniaxial direction.

12. The bio-signal measuring apparatus of claim 11, wherein the pressure sensor comprises at least one strain gauge configured to measure a strain of the substrate, and
    the pressure sensor is configured to measure the contact pressure between the subject and the pulse wave sensor based on the strain measured by the strain gauge.

13. The bio-signal measuring apparatus of claim 12, wherein the substrate is a printed circuit board or a display substrate.

14. The bio-signal measuring apparatus of claim 11, wherein the two holes are formed in parallel on an outside of both ends of the protruding parts.

15. The bio-signal measuring apparatus of claim 12, wherein the at least one strain gauge is provided between the protruding parts.

16. The bio-signal measuring apparatus of claim 12, wherein the pulse wave sensor has a top surface configured to come into direct contact with the subject.

17. The bio-signal measuring apparatus of claim 12, wherein the pulse wave sensor protrudes from a top surface of the substrate.

18. The bio-signal measuring apparatus of claim 12, wherein the strain gauge is provided at a position of the plate that is not in contact with the pulse wave sensor.

19. A bio-signal measuring apparatus comprising:
   a substrate;
   a pulse wave sensor provided in direct contact with the substrate and configured to measure pulse waves of a subject;
   a plate comprising protruding parts which contact a bottom portion of the substrate; and
   a pressure sensor provided at the plate and configured to measure a contact pressure between the subject and the pulse wave sensor;
   wherein the pressure sensor is provided between the protruding parts.

* * * * *